United States Patent
Van Berkel (10) Patent No.: US 11,585,792 B2
(45) Date of Patent: Feb. 21, 2023

(54) OPEN PORT SAMPLING INTERFACE

(71) Applicant: UT-BATTELLE, LLC, Oak Ridge, TN (US)

(72) Inventor: Gary J. Van Berkel, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 17/729,701

(22) Filed: Apr. 26, 2022

(65) Prior Publication Data

US 2022/0373521 A1 Nov. 24, 2022

Related U.S. Application Data (63) Continuation of application No. 17/147,450, filed on Jan. 12, 2021, now Pat. No. 11,313,841, which is a (Continued)

(51) Int. Cl.
*H01J 49/04* (2006.01)
*G01N 30/72* (2006.01)
(Continued)

(52) U.S. Cl.
CPC .......... *G01N 30/7233* (2013.01); *A61B 5/443* (2013.01); *A61B 10/02* (2013.01);
(Continued)

(58) Field of Classification Search
CPC ........ G01N 30/7233; G01N 1/00; G01N 1/20; G01N 35/1095; G01N 2001/028;
(Continued)

(56) References Cited

U.S. PATENT DOCUMENTS

| 3,806,321 A | 4/1974 | Durrum et al. |
| 3,897,213 A | 7/1975 | Stevens et al. |

(Continued)

FOREIGN PATENT DOCUMENTS

| CN | 101652650 A | 2/2010 |
| CN | 101696916 A | 4/2010 |

(Continued)

OTHER PUBLICATIONS

International Search Report and Written Opinion dated Aug. 11, 2016 for International Patent Application No. PCT/US16/26709.

(Continued)

*Primary Examiner* — David J Bolduc
(74) *Attorney, Agent, or Firm* — Fox Rothschild LLP

(57) ABSTRACT

A system for sampling a sample material includes a probe which can have an outer probe housing with an open end. A liquid supply conduit within the housing has an outlet positioned to deliver liquid to the open end of the housing. The liquid supply conduit can be connectable to a liquid supply for delivering liquid at a first volumetric flow rate to the open end of the housing. A liquid exhaust conduit within the housing is provided for removing liquid from the open end of the housing. A liquid exhaust system can be provided for removing liquid from the liquid exhaust conduit at a second volumetric flow rate. A droplet dispenser can dispense drops of a sample or a sample-containing solvent into the open end of the housing. A sensor and a processor can be provided to monitor and maintain a liquid dome present at the open end.

20 Claims, 12 Drawing Sheets

Related U.S. Application Data continuation of application No. 16/806,228, filed on Mar. 2, 2020, now Pat. No. 10,895,559, which is a continuation of application No. 16/058,663, filed on Aug. 8, 2018, now Pat. No. 10,578,593, which is a continuation of application No. 15/839,453, filed on Dec. 12, 2017, now Pat. No. 10,048,236, which is a continuation of application No. 15/474,501, filed on Mar. 30, 2017, now Pat. No. 9,869,661, which is a continuation of application No. 14/682,837, filed on Apr. 9, 2015, now Pat. No. 9,632,066.

(51) Int. Cl.

| | | |
|---|---|---|
| *G01N 1/00* | (2006.01) | |
| *G01N 35/10* | (2006.01) | |
| *A61B 5/00* | (2006.01) | |
| *A61B 10/02* | (2006.01) | |
| *G01N 1/20* | (2006.01) | |
| G01N 30/02 | (2006.01) | |
| G01N 1/02 | (2006.01) | |
| G01N 1/04 | (2006.01) | |

(52) U.S. Cl.
CPC .............. *G01N 1/00* (2013.01); *G01N 1/20* (2013.01); *G01N 35/1095* (2013.01); *H01J 49/0404* (2013.01); *H01J 49/0431* (2013.01); *A61B 5/44* (2013.01); *A61B 5/4845* (2013.01); *G01N 2001/028* (2013.01); *G01N 2001/045* (2013.01); *G01N 2030/027* (2013.01)

(58) Field of Classification Search
CPC ........ G01N 2001/045; G01N 2030/027; A61B 5/443; A61B 10/02; A61B 5/44; A61B 5/4845; H01J 49/0404; H01J 49/0431
See application file for complete search history.

(56) References Cited

U.S. PATENT DOCUMENTS

| | | |
|---|---|---|
| 4,311,586 A | 1/1982 | Baldwin et al. |
| 5,271,798 A | 12/1993 | Sandhu et al. |
| 5,333,655 A | 8/1994 | Bergamini et al. |
| 5,536,471 A | 7/1996 | Clark et al. |
| 5,736,740 A | 4/1998 | Franzen |
| 5,783,938 A | 7/1998 | Munson et al. |
| 5,785,831 A | 7/1998 | Bek |
| 5,935,051 A | 8/1999 | Bell |
| 6,260,407 B1 | 7/2001 | Petro et al. |
| 6,290,863 B1 | 9/2001 | Morgan et al. |
| 6,296,771 B1 | 10/2001 | Miroslav |
| 6,358,692 B1 | 3/2002 | Jindal et al. |
| 6,475,391 B2 | 11/2002 | Safir et al. |
| 6,478,238 B1 | 11/2002 | Wachs et al. |
| 6,677,593 B1 | 1/2004 | Van Berkel |
| 6,784,439 B2 | 8/2004 | Van Berkel |
| 6,803,566 B2 | 10/2004 | Van Berkel |
| 7,295,026 B2 | 11/2007 | Van Berkel et al. |
| 7,525,105 B2 | 4/2009 | Kovtoun |
| 7,995,216 B2 | 8/2011 | Van Berkel et al. |
| 8,003,937 B2 | 8/2011 | Kertesz et al. |
| 8,084,735 B2 | 12/2011 | Kertesz et al. |
| 8,117,929 B2 | 2/2012 | Van Berkel et al. |
| 8,327,725 B2 | 12/2012 | Kanomata |
| 8,384,020 B2 | 2/2013 | Jesse et al. |
| 8,486,703 B2 | 7/2013 | Van Berkel et al. |
| 8,519,330 B2 | 8/2013 | Van Berkel et al. |
| 8,555,709 B2 | 10/2013 | Davison et al. |
| 8,637,813 B2 | 1/2014 | Van Berkel et al. |
| 8,742,338 B2 | 6/2014 | Van Berkel et al. |
| 9,063,047 B2 | 6/2015 | Van Berkel et al. |
| 9,064,680 B2 | 6/2015 | Van Berkel |
| 9,140,633 B2 | 9/2015 | Van Berkel et al. |
| 9,153,425 B2 | 10/2015 | Van Berkel |
| 9,176,028 B2 | 11/2015 | ElNaggar et al. |
| 9,297,828 B2 | 3/2016 | Ovchinnikova et al. |
| 9,390,901 B2 | 7/2016 | Kertesz et al. |
| 9,632,066 B2 | 4/2017 | Van Berkel |
| 2001/0023130 A1 | 9/2001 | Gilton et al. |
| 2003/0066957 A1 | 4/2003 | Andersson et al. |
| 2003/0193020 A1 | 10/2003 | Van Berkel |
| 2004/0021068 A1 | 2/2004 | Staats |
| 2004/0036020 A1 | 2/2004 | Sakairi et al. |
| 2004/0093933 A1 | 5/2004 | Berger et al. |
| 2004/0149053 A1 | 8/2004 | Staphanos |
| 2005/0258361 A1 | 11/2005 | Whitehouse et al. |
| 2007/0046934 A1 | 3/2007 | Roy |
| 2007/0259445 A1 | 11/2007 | Cerda |
| 2008/0128614 A1 | 6/2008 | Nikolaev et al. |
| 2008/0272294 A1 | 11/2008 | Kovtoun |
| 2009/0053689 A1 | 2/2009 | Oviso, Jr. et al. |
| 2009/0101814 A1 | 4/2009 | Amirav |
| 2009/0140137 A1 | 6/2009 | Hiraoka et al. |
| 2009/0314716 A1 | 12/2009 | Osaka |
| 2010/0002905 A1 | 1/2010 | Van Berkel et al. |
| 2010/0019140 A1 | 1/2010 | Amirav et al. |
| 2010/0037919 A1 | 2/2010 | Doebelin et al. |
| 2010/0224013 A1 | 9/2010 | Van Berkel et al. |
| 2011/0036453 A1 | 2/2011 | Ardenkjaer-larsen et al. |
| 2011/0120213 A1 | 5/2011 | Hirayama et al. |
| 2011/0133077 A1 | 6/2011 | Henion et al. |
| 2011/0167898 A1 | 7/2011 | Zhou et al. |
| 2011/0198495 A1 | 8/2011 | Hiraoka |
| 2011/0284735 A1 | 11/2011 | Van Berkel et al. |
| 2012/0053065 A1 | 3/2012 | Van Berkel |
| 2012/0079894 A1 | 4/2012 | Van Berkel et al. |
| 2012/0083045 A1 | 4/2012 | Van Berkel et al. |
| 2014/0096624 A1 | 4/2014 | ElNaggar et al. |
| 2014/0216177 A1 | 8/2014 | Van Berkel et al. |
| 2014/0238155 A1 | 8/2014 | Van Berkel et al. |
| 2015/0226710 A1 | 8/2015 | Hochgraeber |
| 2016/0022189 A1 | 1/2016 | Pouteau et al. |
| 2016/0126080 A1 | 5/2016 | Kertesz et al. |
| 2016/0181078 A1 | 6/2016 | Kovarik |
| 2016/0299041 A1 | 10/2016 | Kertesz et al. |
| 2016/0299109 A1 | 10/2016 | Van Berkel |
| 2017/0248573 A1 | 8/2017 | Sullivan et al. |
| 2017/0315026 A1 | 11/2017 | Andreussi |
| 2017/0316926 A1 | 11/2017 | Arnold et al. |
| 2020/0043712 A1 | 2/2020 | Arnold et al. |

FOREIGN PATENT DOCUMENTS

| | | |
|---|---|---|
| CN | 102414778 A | 4/2012 |
| CN | 102759466 | 10/2012 |
| CN | 102759466 A | 10/2012 |
| CN | 104165778 A | 11/2014 |
| EP | 0211645 A2 | 2/1987 |
| EP | 0898977 A2 | 3/1999 |
| EP | 1623204 A1 | 2/2006 |
| EP | 1909090 A2 | 4/2008 |
| JP | 2004340646 A | 12/2004 |
| JP | 2011210734 A | 10/2011 |
| JP | 2011232180 A | 11/2011 |
| JP | 2012-519847 A | 8/2012 |
| JP | 2013526700 A | 6/2013 |
| WO | 0019193 A1 | 4/2000 |
| WO | 2011140492 | 10/2011 |

OTHER PUBLICATIONS

Tycova et al.: "Capillary electrophoresis in an extended nanospray tip-electrosprayas an electrophoretic column", J. Chromatogr. A 1388 (2015) 274-279.

Liu et al.: "A Falling Drop for Sample Injection in Capillary Zone Electrophoresis", Anal. Chem. Mar. 1997, vol. 69, 1211-1216.

Ovchinnikova et al., "Transmission geometry laser ablation into a non-contact liquid vortex capture probe for mass spectrometry imaging", Rapid Commun. Mass Spectrom. 2014, 28, 1665-1673.

International Search Report dated Jul. 1, 2016 in PCT/US2016/026706.

(56) References Cited

OTHER PUBLICATIONS

Gary J. Van Berkel et al: "An open port sampling interface for liquid introduction atmospheric pressure ionization mass spectrometry: Open port sampling interface", Rapid Communications in Mass Spectrometry., vol. 29, No. 19, Oct. 15, 2015 (Oct. 15, 2015), pp. 1749-1756.
Extended European Search Report dated Nov. 7, 2018 in 16777383.7.
Extended European Search Report dated Nov. 13, 2018 in EP 1677385.2.
International Search Report dated Apr. 24, 2019 in PCT/US19/15894.

OPEN PORT SAMPLING INTERFACE

CROSS REFERENCE TO RELATED APPLICATIONS

This application is a continuation application of U.S. application Ser. No. 17/147,450 filed Jan. 12, 2021, which is a continuation of U.S. application Ser. No. 16/806,228 filed on Mar. 2, 2020, which issued as U.S. Pat. No. 10,895,559 on Jan. 19, 2021, which is a continuation application of U.S. application Ser. No. 16/058,663 filed on Aug. 8, 2018, which issued as U.S. Pat. No. 10,578,593 on Mar. 3, 2020, which is a continuation application of U.S. application Ser. No. 15/839,453, filed Dec. 12, 2017, which issued as U.S. Pat. No. 10,048,236 on Aug. 14, 2018, which is a continuation application of U.S. application Ser. No. 15/474,501 filed on Mar. 30, 2017, which issued as U.S. Pat. No. 9,869,661 on Jan. 16, 2018, which is a continuation application of U.S. application Ser. No. 14/682,837, filed Apr. 9, 2015, which issued as U.S. Pat. No. 9,632,066 on Apr. 25, 2017, and is related to PCT application no. PCT/US16/26709, filed on Apr. 8, 2016, all entitled "OPEN PORT SAMPLING INTERFACE", the disclosures of which are hereby incorporated herein fully by reference in their entireties.

STATEMENT REGARDING FEDERALLY SPONSORED RESEARCH

This invention was made with government support under contract No. DE-AC05-00OR22725 awarded by the U.S. Department of Energy. The government has certain rights in this invention.

FIELD OF THE INVENTION

This invention relates generally to sample analysis systems and methods, and more particularly to sample analysis systems utilizing sampling probes.

BACKGROUND OF THE INVENTION

The proper sampling of sample materials and preparation of such materials for further chemical analysis can present challenges. In the case of mass spectrometry and high performance liquid chromatography, for example, the sample must be properly placed into solution prior to entering the analysis device. The sample material can be received in diverse forms such as particulates ejected from a solid sample surface by laser or acoustic ablation, as a solid from puncture sampling devices such as pins, from droplets of sample-bearing solution, from liquid extraction from a surface, and the like. These sample specimens must be processed into an appropriate solution prior to further chemical analysis. This can require additional steps and complicates and prolongs the time required to perform the analysis. Also, the testing can involve multiple or repeated samples and requires these steps to be repeated and the equipment required to place the sample into solution to be washed or replaced repeatedly.

SUMMARY OF THE INVENTION

A system for sampling a sample material includes a probe comprising an outer probe housing with an inner wall and an open end. A liquid supply conduit within the housing has an outlet positioned to deliver liquid to the open end of the housing. The liquid supply conduit can be connectable to a liquid supply for delivering liquid at a first volumetric flow rate to the open end of the housing. A liquid exhaust conduit within the housing is provided for removing liquid from the open end of the housing. A liquid exhaust system in fluid connection with the liquid exhaust conduit can be provided for removing liquid from the liquid exhaust conduit at a second volumetric flow rate, the first volumetric flow rate exceeding the second volumetric flow rate, wherein liquid at the open end will receive sample, liquid containing sample material will be drawn into and through the liquid exhaust conduit, and liquid will overflow from the open end of the probe. The first volumetric flow rate can be at least 5% greater than the second volumetric flow rate. The liquid exhaust system can include a connection for placing the liquid exhaust conduit in liquid communication with a chemical analysis device.

The system can further include an overflow collection system for collecting the overflow liquid from the open end of the probe. The collection system can be a collection container surrounding the outer probe housing. The liquid exhaust system can include a connection for placing the liquid exhaust conduit in liquid communication with a chemical analysis device, and can further include a processor. The processor can receive a signal from a chemical analysis device if a sample of interest is present in in liquid from the liquid exhaust system. The processor can then direct the collection of overflow liquid. The collection system can include a connection for placing overflow liquid collected by the collection system in liquid communication with a chemical analysis device.

A method for sampling a sample material can include the step of providing a probe including an outer probe housing having an inner wall and an open end, a liquid supply conduit within the housing having an outlet positioned to deliver liquid to the open end of the housing, and an exhaust conduit within the housing for removing liquid from the open end of the housing. A liquid exhaust system can be provided in fluid connection with the liquid exhaust conduit for removing liquid from the liquid exhaust conduit. Liquid is flowed through the liquid supply conduit to deliver liquid at a first volumetric flow rate to the open end of the housing. Liquid is flowed through the liquid exhaust system at a second volumetric flow rate. The first volumetric flow rate can exceed the second volumetric flow rate, wherein liquid at the open end will receive sample, liquid containing the sample will be drawn into and through the liquid exhaust conduit, and liquid will overflow from the open end. The first volumetric flow rate can be at least 5% greater than the second volumetric flow rate The method can further include the step of performing chemical analysis on liquid from the liquid exhaust system. The chemical analysis can be at least one selected from the group consisting of high performance liquid chromatography and mass spectrometry.

The method can include providing a liquid overflow collection system, and further can include the step of collecting overflow liquid with the collection system. Overflow liquid from the collection system can be directed to a chemical analysis device. The method can include the step of performing chemical analysis on liquid from the liquid exhaust system, and if an analyte of interest is detected in the chemical analysis, can further include the step of collecting overflow liquid.

A probe for sampling a sample material can include an outer probe housing having an inner wall and an open end, a liquid supply conduit within the housing and having an outlet positioned to deliver liquid to the open end of the housing, and an exhaust conduit within the housing for removing liquid from the open end of the housing. The liquid supply conduit can be connectable to a liquid supply for delivering liquid at a first volumetric flow rate to the open end of the housing. The liquid exhaust conduit can be connectable to a liquid exhaust system for removing liquid from the liquid exhaust conduit at a second volumetric flow rate. The first volumetric flow rate in a first mode of operation can exceed the second volumetric flow rate, wherein liquid at the open end will receive sample, liquid containing the sample will be withdrawn from the liquid exhaust conduit, and liquid will overflow from the open end. The probe can further include a collection system for collecting the overflow liquid from the open end of the probe. The collection system can include a container surrounding the outer probe housing.

BRIEF DESCRIPTION OF THE DRAWINGS

There are shown in the drawings embodiments that are presently preferred it being understood that the invention is not limited to the arrangements and instrumentalities shown, wherein:

FIGS. 10A, 10B and 10C were obtained from the sampling of skin with CUDERM® tape strips from both a coffee drinker and a person that had abstained from coffee and other caffeinated beverages for several days prior to the sampling.

FIGS. 11A and 11B show the data from the analysis of a polyethylene terephthalate (PET, 98.5 wt %) color chip that was prepared containing the oil soluble dye solvent green 28 (0.5 wt %) and ethylene bis (stearamide) (EBS) wax (1.0 wt %).

FIGS. 12A, 12B and 12C show the data obtained by dropping droplets (six replicate droplets for each verapamil concentration) of a liquid solution containing the analyte verapamil (0.01-10 micromolar) and the internal standard propranolol (1.0 micromolar) onto the probe liquid dome.

DETAILED DESCRIPTION OF THE INVENTION

Figure 1:
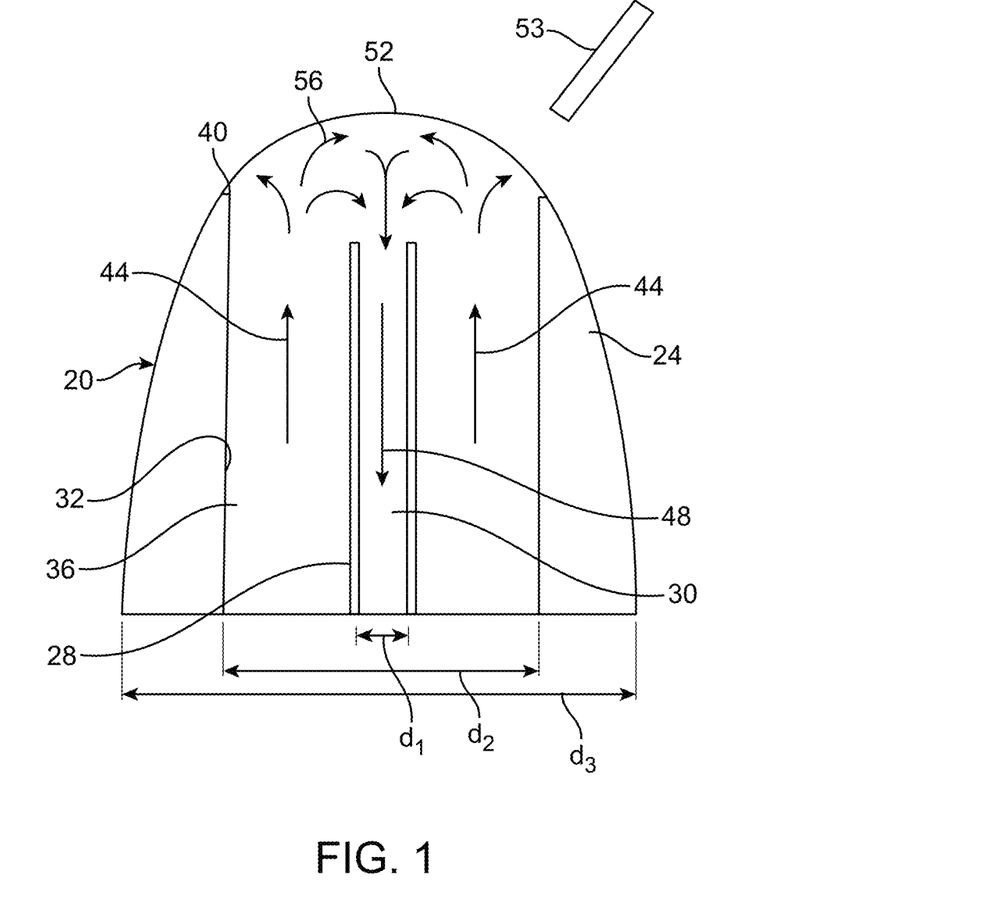
FIG. 1 is a schematic diagram of the open port end of a probe.

A system for sampling a sample material includes a probe 20 comprising an outer probe housing 24 with an inner wall 32 and an open end 40. A liquid supply conduit 36 within the housing 24 has an outlet positioned to deliver liquid to the open end of the housing. The liquid supply conduit 36 can be connectable to a liquid supply for delivering liquid at a first volumetric flow rate to the open end of the housing, as shown by arrow 44. A liquid exhaust flow channel 30 can be defined by a liquid exhaust conduit 28 within the housing and is provided for removing liquid from the open end 40 of the housing 24. A liquid exhaust system in fluid connection with the liquid exhaust conduit 28 can be provided for removing liquid as shown by arrow 48 from the liquid exhaust flow conduit 28 and flow channel 30 at a second volumetric flow rate, the first volumetric flow rate exceeding the second volumetric flow rate, wherein liquid at the open end 40 will receive sample, liquid containing sample material will be drawn into and through the liquid exhaust conduit 28, and liquid will overflow from the open end 40. A dome 52 of liquid will be formed when the liquid supply exceeds the liquid exhaust. Liquid not overflowing the open end 40 will transition from the liquid supply conduit 36 to the liquid exhaust conduit 28 as indicated by arrows 56.

Liquid at the open end 40 will receive sample from a sample material. The sample will be captured in the liquid dome 52. Some of the sample will flow with the liquid through the liquid exhaust conduit 28. The liquid exhaust conduit 28 can be connected to a liquid exhaust system which can deliver the sample and solvent to a suitable chemical analysis device, such as a high performance liquid chromatography (HPLC) device or a mass spectrometer.

The particular arrangement of the liquid supply conduit 36 and the liquid exhaust conduit 28 can be varied. In FIG. 1 the liquid exhaust conduit 28 is provided as a tubular conduit positioned with the outer housing 24, and the liquid supply conduit 36 is defined by the annular space between the liquid exhaust conduit 28 and the inner wall 32 of the outer housing 24. The probe can be differently configured, for example by the provision of one or more tubular liquid supply conduits, by one or more differently constructed liquid exhaust conduits, and the like. The number, geometry, size and relative positioning of the liquid supply conduits and the liquid exhaust conduits can vary, so long as a sufficient quantity of liquid can be delivered to the open end and a sufficient quantity of liquid can be removed by the liquid through the probe to produce the dome 52 and overflow condition when desired, and possibly also a no overflow condition. The dimension of the flow channels can vary. The dimensions of the liquid exhaust flow channel 30, $d_1$, of the liquid supply conduit 28, $d_2$, and of the outer diameter of the housing 24, $d_3$, can all be varied depending on the characteristics of the probe 20 that are desired and the testing to be performed.

The height of the dome 52 will depend on a number of factors including the flow conditions and the solvent. The height of the dome 52 can vary so long as the dome 52 extends beyond the open end 40 of the probe such that sample can be introduced into the probe 20 merely by touching down on the dome 52. The over flow condition in which the liquid supply exceeds the liquid exhaust such that liquid spills over the open end 40 can perform a number of functions. It can allow for the dilution of sample flowing through the liquid exhaust to a desired level, even to the extent of a great excess of liquid overflow. It can perform a cleaning or washing function of the open end 40 of the probe 20. The overflow liquid can also be collected and analyzed separately or recombined in a feedback with the liquid exhaust. It is also possible that the overflow liquid is the primary sample-bearing liquid to be analyzed, and the liquid exhaust is used primarily to control the flow rate of the overflow liquid.

A suitable sensor such as light-based sensor 53 can be used to monitor the dome 52 to establish the correct flow balance. The sensor 53 can provide a signal to a suitable processor which can control valves and the liquid supply and exhaust flow rates.

The first volumetric flow rate can exceed the second volumetric flow rate by any suitable amount. The first volumetric flow rate can be at least 5% greater than the second volumetric flow rate. The first volumetric flow rate can exceed the second volumetric flow rate by several fold, such as 100% or even 1000% if dilution of the sample or cleaning of the open end is desired. The probe can also be operated in a condition where no liquid flows out of the open end. It is also possible that the system could additionally be operated in an underflow condition where the first volumetric flow rate is less than the second volumetric flow rate. Such an operation is disclosed in a copending United States patent application entitled "Capture Probe" and filed on even date herewith, the disclosure of which is fully incorporated by reference.

Figure 2:
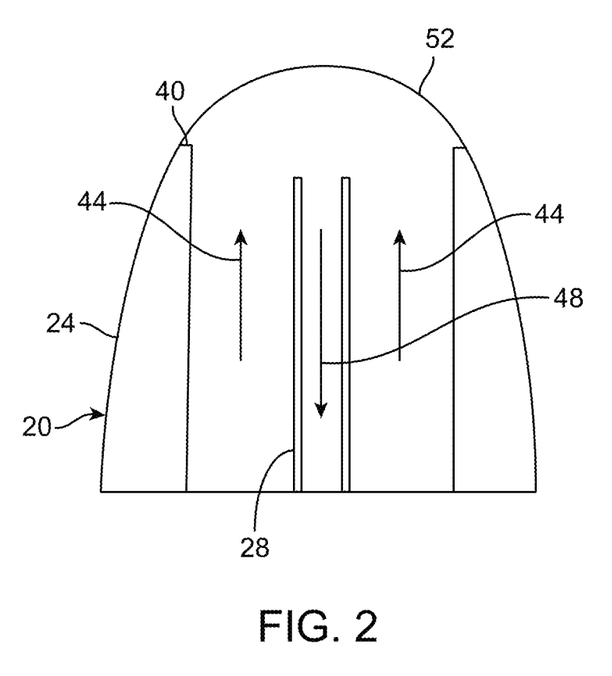
FIG. 2 is a schematic diagram of the probe in the first mode of operation.
Figure 3:
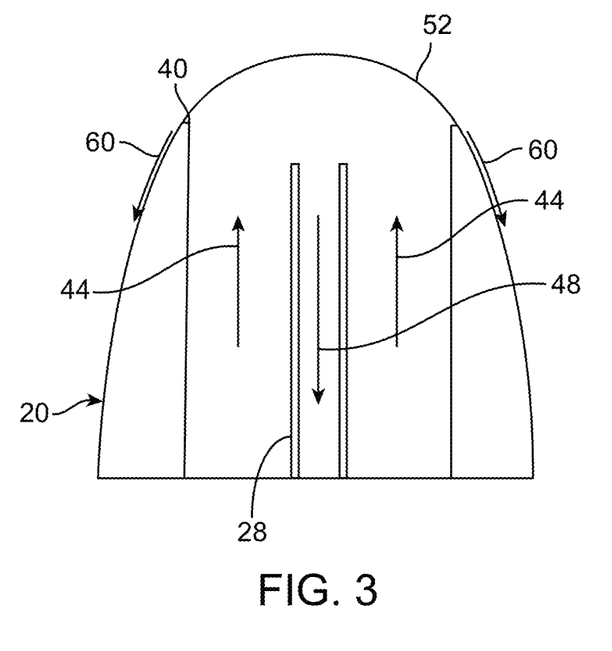
FIG. 3 is a schematic diagram of a probe in a second mode of operation.

There is shown in FIG. 2 the probe 20 being operated in a no overflow or low overflow condition. The volumetric flow rate of the liquid supply and the liquid exhaust are balanced such that little or no liquid overflows the open end 40. There is shown in FIG. 3 the probe 20 being operated in the overflow condition. The volumetric flow rate of liquid supply as indicated by arrows 44 sufficiently exceeds the volumetric flow rate of liquid exhaust as indicated by arrows 48 that a substantial flow of liquid overflows the open end 40, as indicated by arrows 60.

Figure 4:
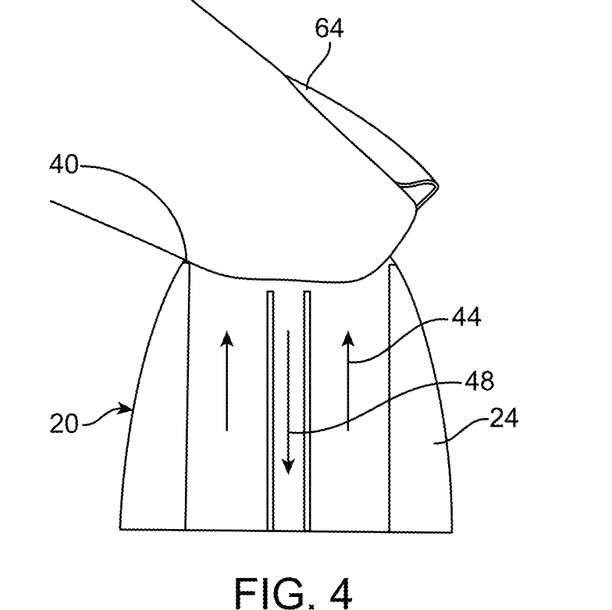
FIG. 4 is a schematic diagram of a probe in a third mode of operation.

There is shown in FIG. 4 a mode of operation wherein an object to be tested such as finger 64 simply touches or in this case completely seals the open end 40. Contact between the object and the solvent will remove sample from the finger, which will flow out of the probe 20 with the liquid exhaust 48 where it can be chemically tested. The probe 20 can return to an overflow condition when the finger is removed to effect cleaning of the open end 40 if desired.

Figure 5:
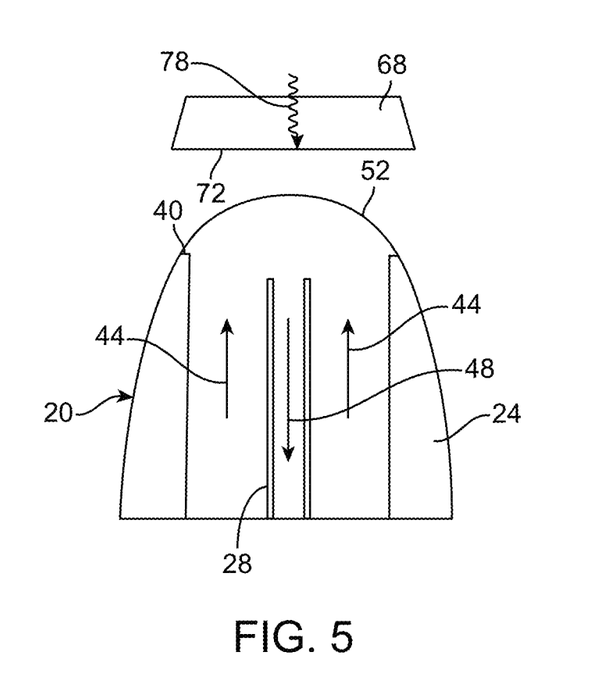
FIG. 5 is a schematic diagram of a probe in a fourth mode of operation.

There is shown in FIG. 5 a mode of operation in which the sample 72 is provided on a sample support 68. The sample 72 is removed by any suitable means, wherein it will fall or otherwise move into contact with the dome 52 of liquid at the open end 40 of the probe 20. In one aspect the support can be transparent to a wavelength of laser light 78 such that the transmitted laser beam 78 ablates the some sample from the sample material 72 on the support 68. Other means for removing sample such as acoustic ablation, reflection laser-induced ablation, and heat or other radiant energy are possible. A device for radiating energy such as an acoustic desorption device can be utilized wherein a laser or other energy imparting device is used to generate an acoustic wave which travels through the sample support to impart energy to the sample and eject sample from the sample material. The acoustic desorption can be laser induced acoustic desorption. The invention can be used with other means for ejecting sample material from the sample to the probe. The sample material can be particulates which are ejected into or fall into the probe, or airborne and diffuse to the probe or are guided to the probe by a guiding gas flow.

Figure 6:
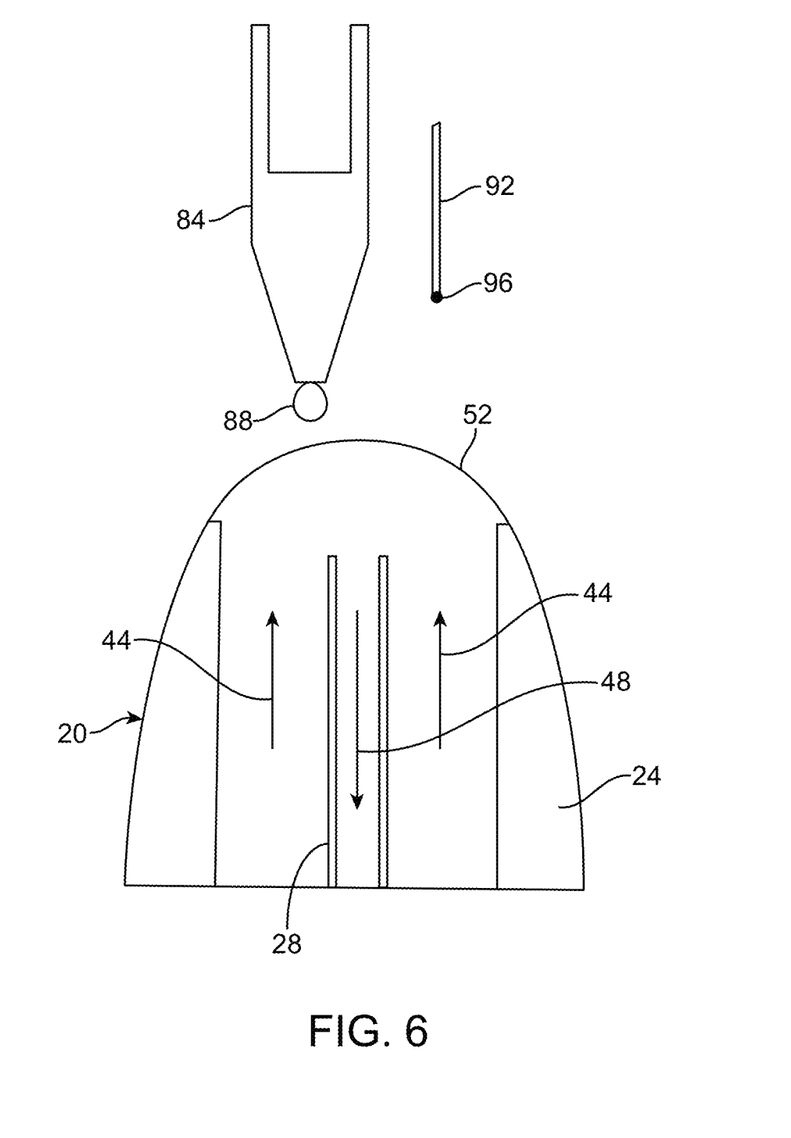
FIG. 6 is a schematic diagram of a probe in a fifth mode of operation.

Any suitable means for delivering sample to the liquid dome 52 are possible. There is shown in FIG. 6, for example an embodiment wherein a droplet dispenser 84 supplies droplets 88 of sample or sample-containing solvent to the dome 52 of the probe 20. The droplet dispenser can also inject sample directly into the solvent dome of the probe. Alternatively a sample 96 can be provided on a sample pin 92 which can be introduced into the solvent dome 52.

The position of the liquid exhaust conduit and the liquid overflow can vary. The position of the liquid exhaust conduit 28 within the outer housing 24 can be used as another variable to control the performance of the probe 20 and the system. In general, the lower the position of the exhaust conduit the greater the extent of sample dilution and the longer the wash through time for a sample.

Figure 7:
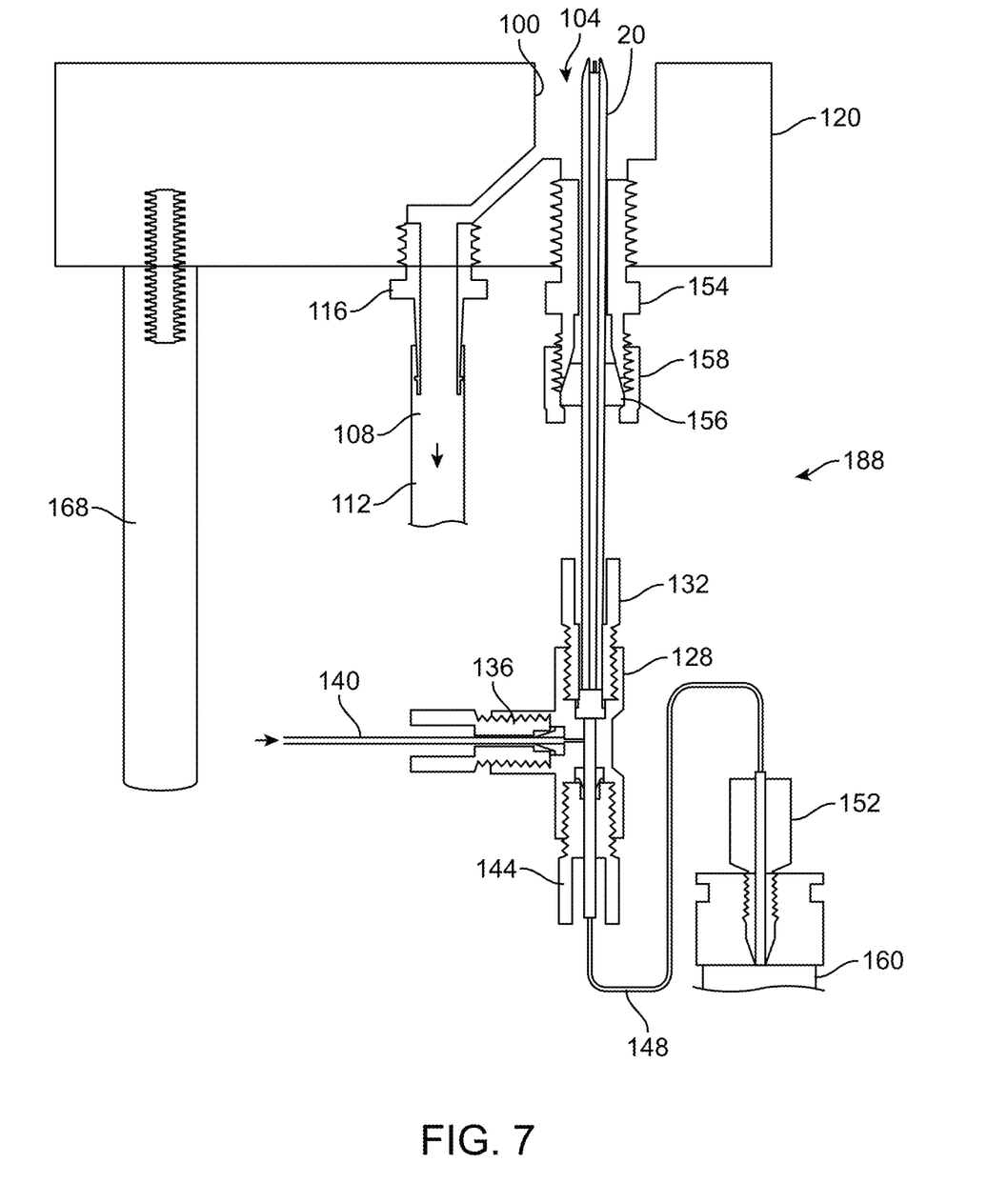
FIG. 7 is a schematic diagram of a probe for sampling of a sample material and having an overflow collection system.

The system can further include an overflow collection system for collecting the overflow liquid from the open end of the probe, as shown in FIG. 7. The collection system can be a collection container 100 surrounding the outer housing of the probe 20. The collection container 100 has an open end 104 by which overflow liquid can flow into the collection container 100. The collection container 100 can be formed in any suitable fashion, size, shape, or material. In the embodiment shown, the collection container 100 is formed in a base 120 to which the probe 20 is mounted. The collection container 100 can communicate with a conduit 112 providing a liquid flow path 108 for removing overflow liquid from the container 100. The conduit 112 can be secured to the base 120 by a suitable fitting 116. A support 168 for the base 120 can be provided.

The system can deliver to and remove solvent from the probe 20 by any suitable means. A liquid intake line 140 receives liquid from a suitable source such as a container or a liquid supply line. A pump such as an HPLC pump (not shown) can be used to meter solvent flow into the probe 20. The liquid can be any suitable solvent for the sample material, such as water, methanol or acetonitrile. Other solvents are possible. A T-connection 128 can include a fitting 132 to engage the probe 20 and make a fluid connection with fitting 136 and between the liquid supply line 140 and the liquid supply conduit 36. A fitting 144 can make a connection between the liquid exhaust conduit 28 and the liquid exhaust line 148. The exhaust line 148 can be connected to inlet 160 of a chemical analysis device such as a mass spectrometer as by a fitting 152. The probe 20 can be connected to the base 120 by any suitable structure such as fitting 154, bushing 156, and securing nut 158. Other connection materials and methods are possible.

Figure 8:
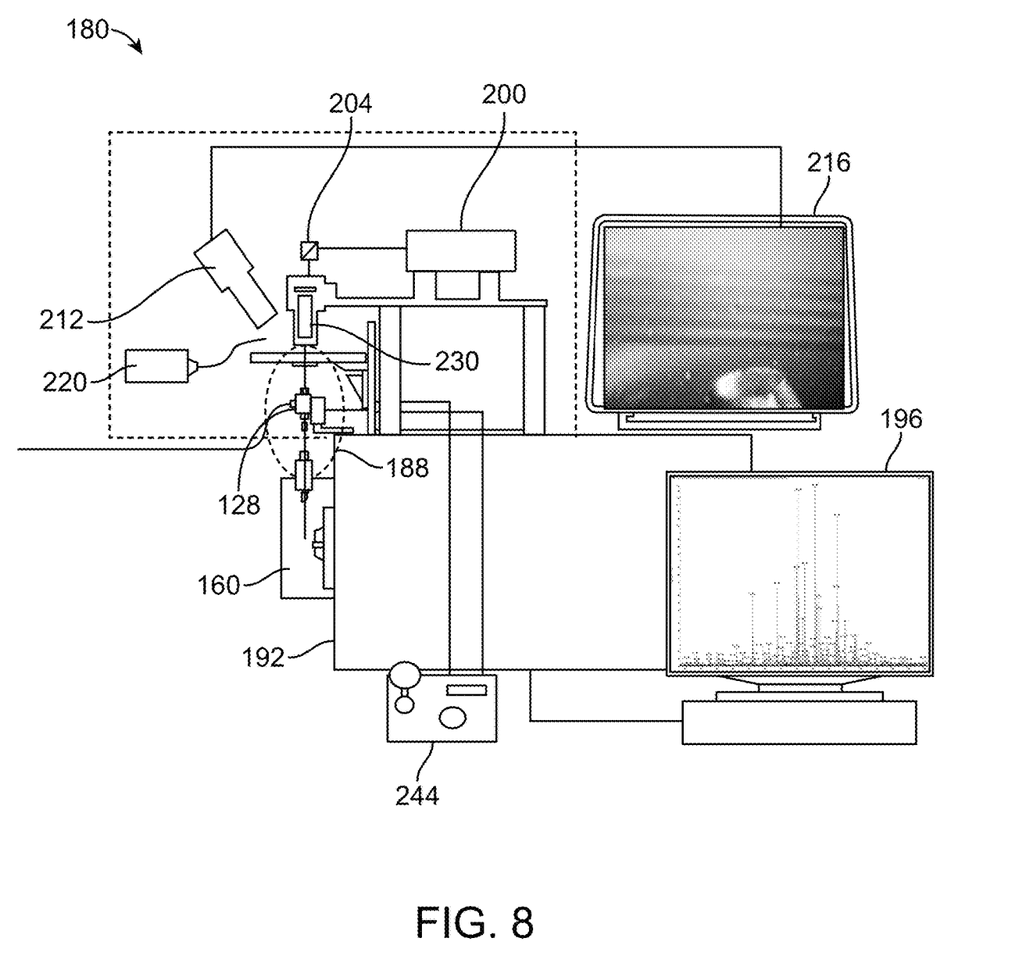
FIG. 8 is a schematic diagram of a system for sampling a sample material.

FIG. 8 is a schematic diagram of a system 180 for sampling a surface. The system 180 can have a sample analysis area 188 including the probe 20, fitting 128 and line 160 to deliver liquid exhaust to a chemical analysis device. A source of radiant energy such as laser 200 can be provided if the means for delivering sample to the probe is laser ablation. If not another suitable device for delivering sample to the probe 20 such as an acoustic ablation device, a droplet dispenser or any suitable device can be used. The system 180 can have other features. A 90 degree prism 204 can be provided to direct the laser beam through a microscope objective 230. A light source 220 can be provided. A video monitor 212 can be provided and can be connected to a display 216. A mass spectrometer 192 or other chemical analysis device can be provided and can have a monitor 196 and a suitable control 244 such as a joystick, processor or other control device.

A processor can be provided to control operation of the device, and particularly the flow rates of the liquid supply, liquid exhaust and overflow as desired. The processor can also control the operation of the sample-supplying device such as the laser 200. The processor can receive sensor signals and provide control signals to suitable valves and control circuitry to control operation of these devices and the system in general. The processor can receive a signal from a chemical analysis device if a sample of interest is present in the liquid from the liquid exhaust system. The processor can then direct the collection of overflow liquid. The collection system can include a connection for placing overflow liquid collected by the collection system in liquid communication with a chemical analysis device.

The method can further include the step of performing chemical analysis on liquid from the liquid exhaust system. The chemical analysis can be at least one selected from the group consisting of high performance liquid chromatography and mass spectrometry. The analytical instrument for example can be any instrument utilized for analyzing analyte solutions. Exemplary analytical instruments include, but are not limited to, mass spectrometers, ionization sources, spectroscopy devices, separation methods, and combinations thereof. Exemplary ionization sources include, but are not limited to electrospray ionization (ESI), atmospheric pressure chemical ionization (APCI), electrospray chemical ionization (ESCi), atmospheric pressure photo-ionization (APPI) or inductively coupled plasma (ICP). Exemplary separation methods include, but are not limited to liquid chromatography, solid phase extraction, HPLC, capillary electrophoresis, or any other liquid phase sample cleanup or separation process. Exemplary mass spectrometers include, but are not limited to, sector time-of-flight, quadrupole mass filter three-dimensional quadrupole ion trap, linear quadrupole ion trap, Fourier transform ion cyclotron resonance orbitrap and toroidal ion trap.

Figure 9A:
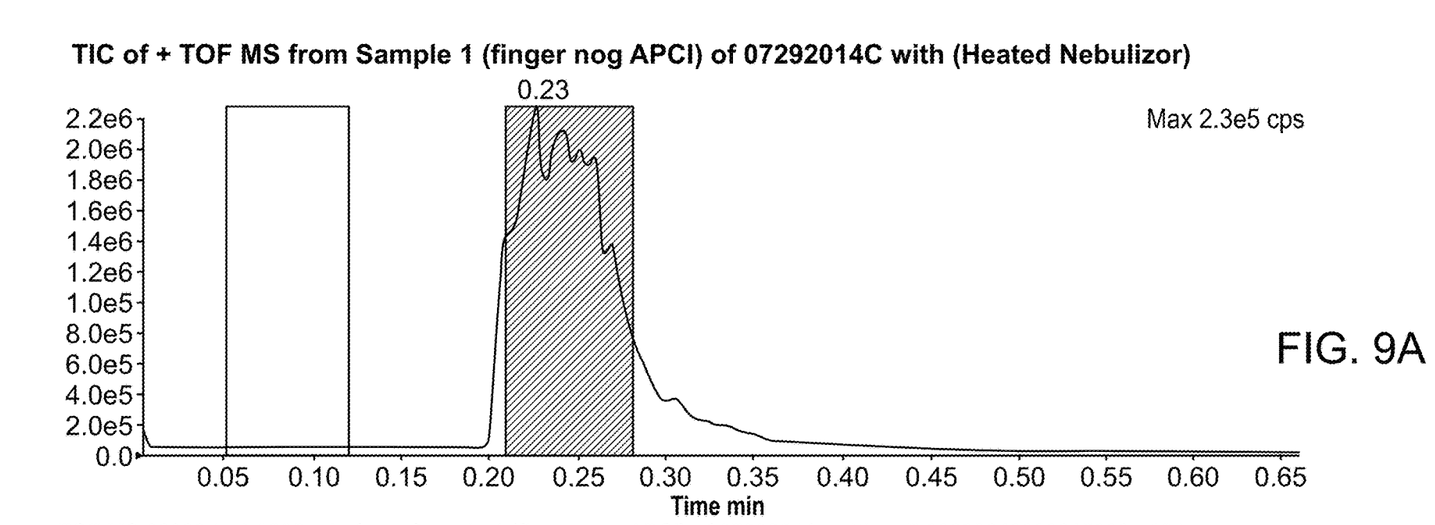
FIG. 9A is the total ion current (TIC) chronogram recorded after touching a fingertip to the open end of the open sampling interface of the probe for 5 s.
Figure 9B:
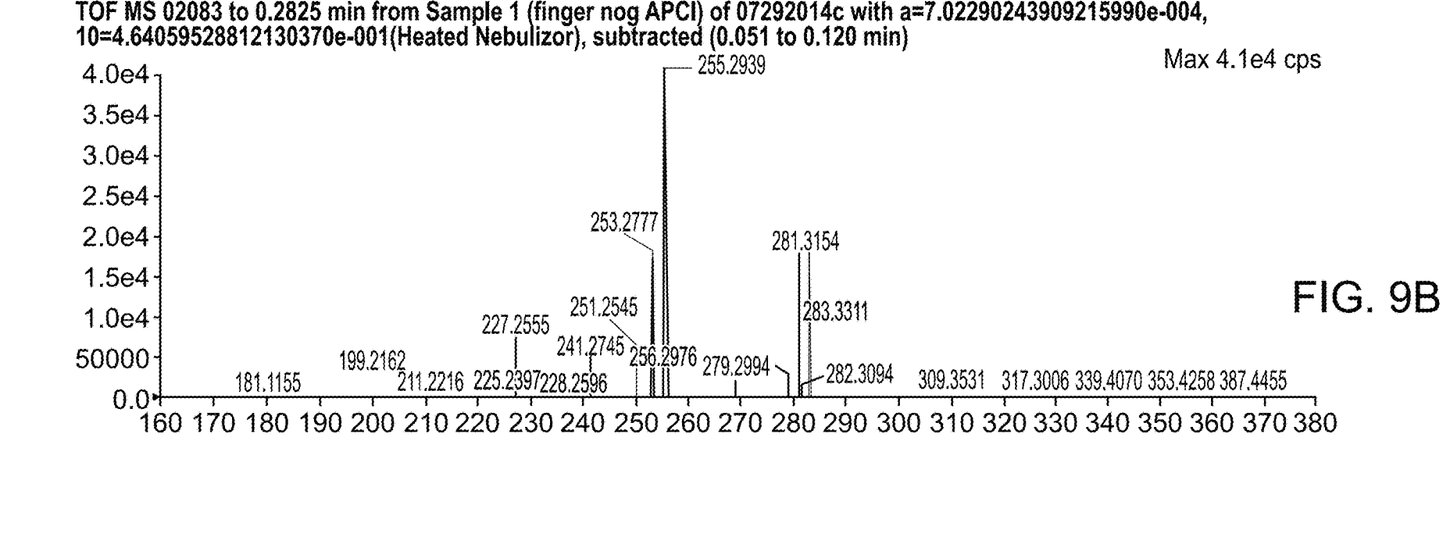
FIG. 9B shows the averaged and background subtracted full scan mass spectrum obtained from this sampling. Sample and background signals are indicated by the greyed areas in FIG. 9A.

FIG. 9A is the total ion current (TIC) chronogram recorded after touching a fingertip to the solvent interface dome at the open end of the probe for 5 s. The rise and fall in signal between 0.20 minutes and 0.35 minutes is due to the material from the fingered extracted from and sampled into the exhaust conduit of the probe and on to the analysis device in this case a time of flight mass spectrometer using negative ion mode APCI. The probe was operated with 350 µL/min methanol in overflow mode. FIG. 9B shows the averaged and background subtracted full scan mass spectrum obtained from this sampling. Sample and background signals are indicated by the greyed areas in FIG. 9A. The main peaks in the spectrum area identified as the most abundant fatty acids known to be present in skin, viz., myristoleic acid (m/z 225), myristic acid (m/z 227), palmitoleic acid (m/z 253), palmitic acid (m/z 255), linoleic acid (m/z 279) and oleic acid (m/z 281).

Figure 10A:
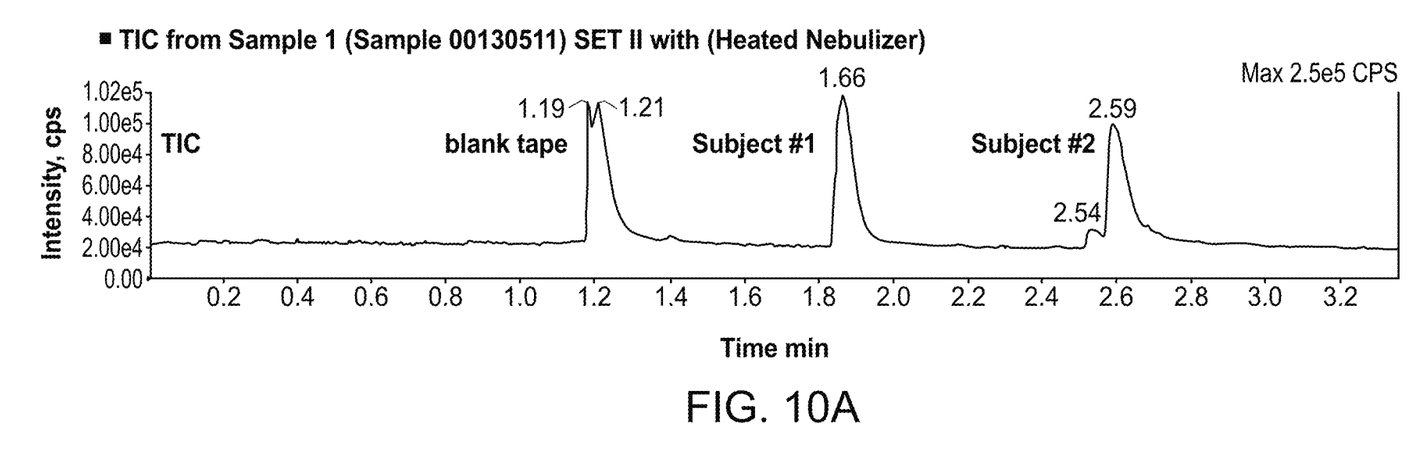
FIG. 10A is the total ion current (TIC) chronogram recorded after touching a blank tape and the tape that sampled the skin of subject #1 and subject #2 to the sampling interface of the probe for 5 s.
Figure 10B:
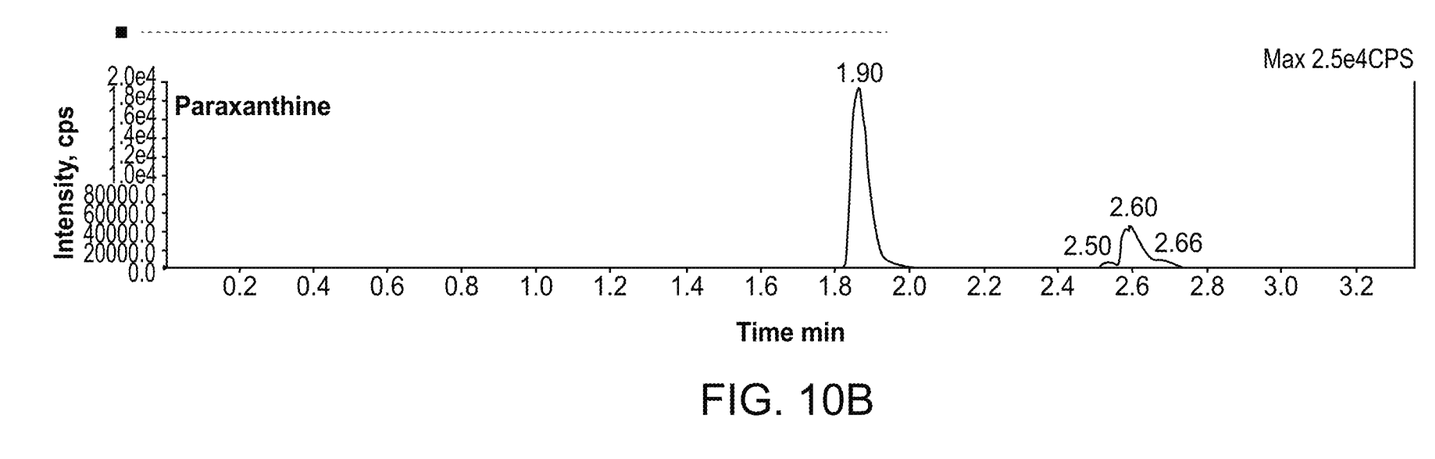
FIG. 10B is that chronogram signal extracted from the TIC that is specific for the caffeine metabolite paraxanthine.
Figure 10C:
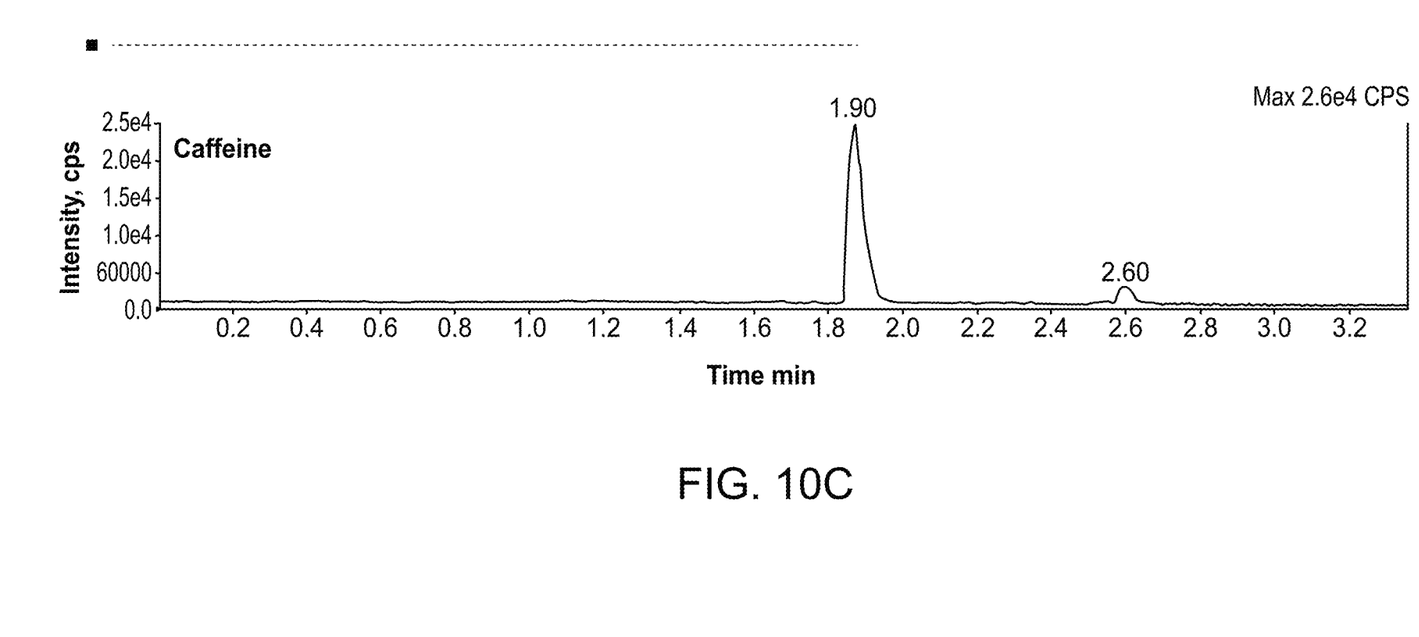
FIG. 10C is that chronogram signal extracted from the TIC that is specific for caffeine.

The data of FIGS. 10A, 10B and 10C were obtained from the sampling of skin with CUDERM® tape strips from both a coffee drinker and a person that had abstained from coffee and other caffeinated beverages for several days prior to the sampling. FIG. 10A is the total ion current (TIC) chronogram recorded after touching a blank tape and the tape that sampled the skin of subject #1 and subject #2 to the solvent dome at the open end of the probe for 5 s. The rise and fall in signal for each sampling is due to the material from the tape being extracted from and sampled into the exhaust conduit of the probe and on to the analysis device in this case a time of flight mass spectrometer using positive ion mode APCI. The probe was operated with 350 µL/min methanol in overflow mode. FIG. 10B is that chronogram signal extracted from the TIC that is specific for the caffeine metabolite paraxanthine. FIG. 10C is that chronogram signal extracted from the TIC that is specific for caffeine. The presence of caffeine and related product paraxanthine is clearly evident for subject #1, the known coffee drinker, and was about 3 orders of magnitude lower in the sample from subject #2 who abstained from consuming caffeine for several days prior to the sampling.

Figure 11A:
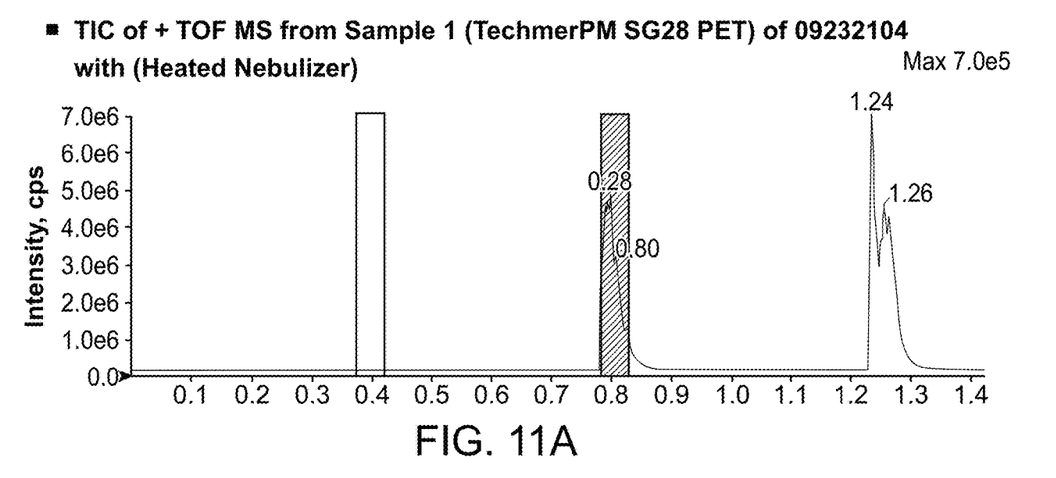
FIG. 11A is the total ion current (TIC) chronogram recorded after touching the PET color chip to the sampling interface of the probe for 1 s.
Figure 11B:
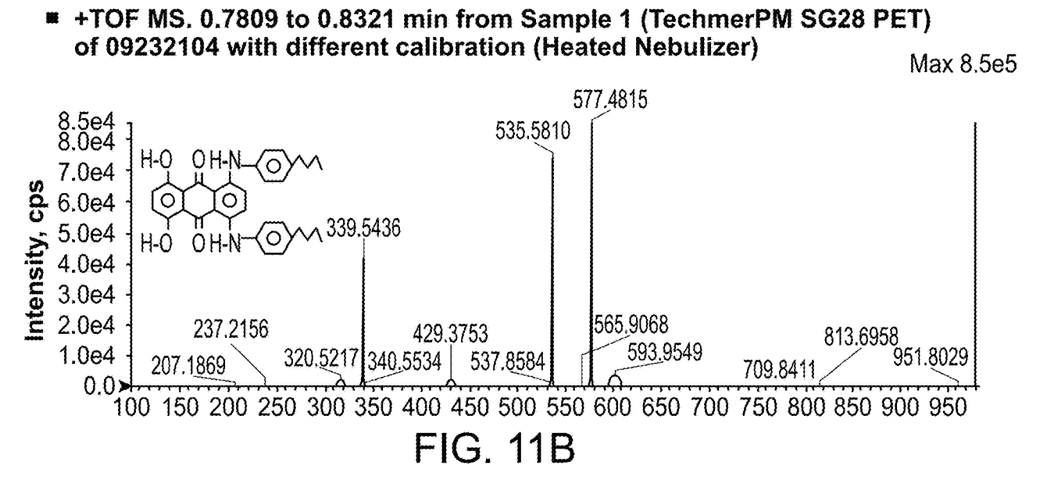
FIG. 11B shows the averaged and background subtracted full scan mass spectrum obtained from the first of the two samplings. Sample and background signals are indicated by the greyed areas in FIG. 11A.

FIGS. 11A and 11B show the data from the analysis of a polyethylene terephthalate (PET, 98.5 wt %) color chip that was prepared containing the oil soluble dye solvent green 28 (0.5 wt %) and ethylene bis (stearamide) (EBS) wax (1.0 wt %). FIG. 11A is the total ion current (TIC) chronogram recorded after touching the PET color chip to the solvent dome at the open end of the probe for 1 s. The rise and fall in signal for each of two samplings is due to the material from the plastic being dissolved and extracted from and sampled into the exhaust conduit of the probe and on to the analysis device in this case a time of flight mass spectrometer using positive ion mode APCI. The probe was operated with 350 µL/min methanol/chloroform (1/1 v/v) in overflow mode. FIG. 11B shows the averaged and background subtracted full scan mass spectrum obtained from the first of the two samplings. Sample and background signals are indicated by the greyed areas in FIG. 11A. The main peaks in the spectrum area are identified as components of the PET (PET dimer-$(CH_2)_2O$ at m/z 338 and a PET trimer at m/z 577) and the known additives solvent green 28 ($(M+H)^+$ at m/z 535) and EBS wax peaks at m/z 538, 566 and 594.

Figure 12A:
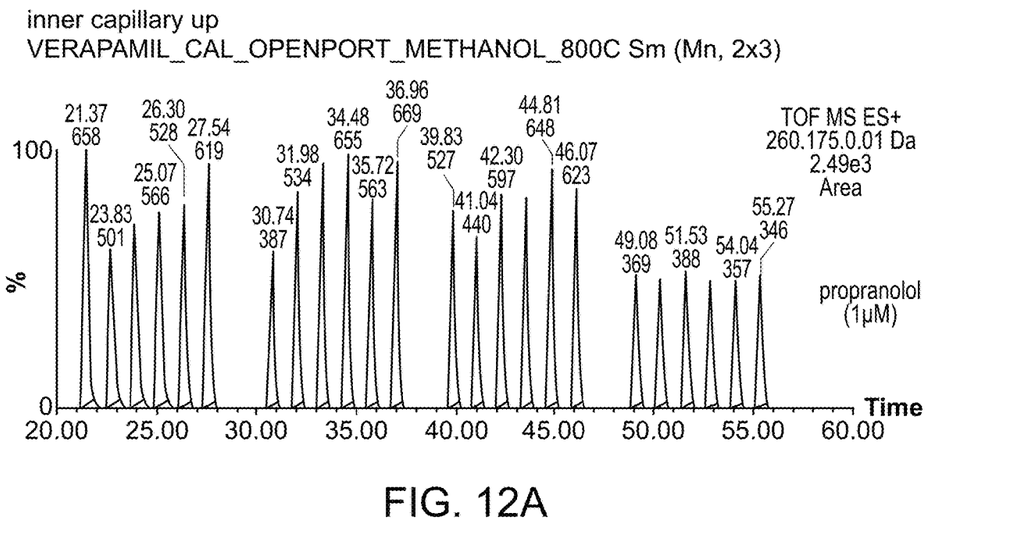
FIG. 12A is the resulting extracted ion current chronogram for propranolol and FIG. 12B is the resulting extracted ion current chronogram for verapamil. The plot of the ratio of the integrated peak area of verapamil to propranol was curve fitted demonstrating quantitative analysis capabilities (FIG. 12C).
Figure 12B:
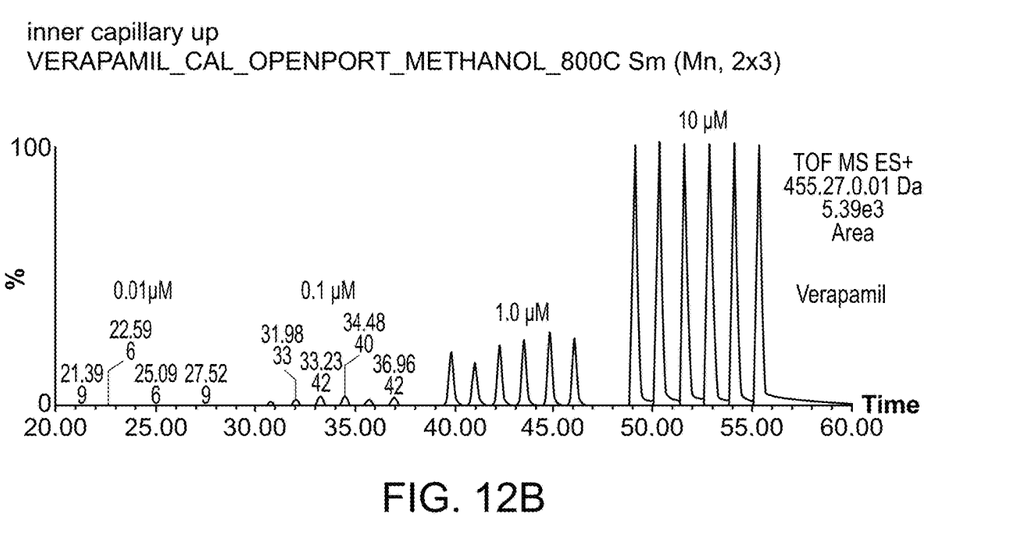
Figure 12C:
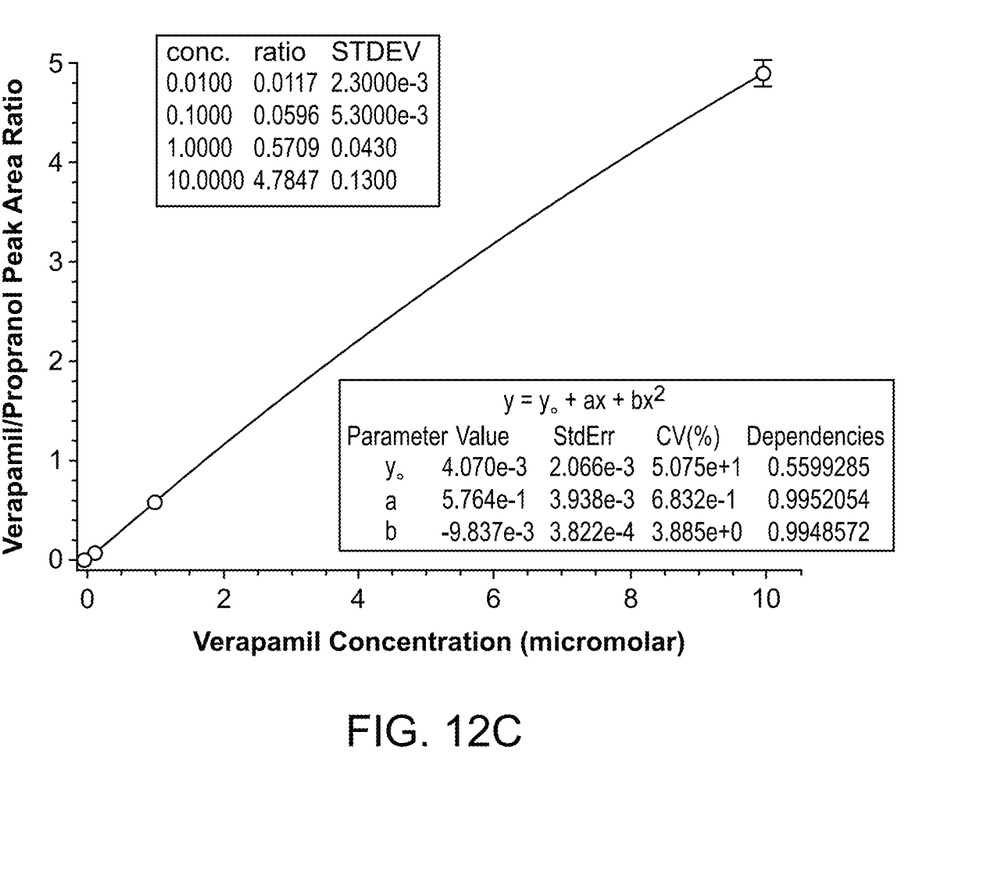

FIGS. 12A, 12B and 12C show the data obtained by dropping droplets (six replicate droplets for each verapamil concentration) of a liquid solution containing the analyte verapamil (0.01-10 micromolar) and the internal standard propranolol (1.0 micromolar) onto the probe liquid dome. FIG. 12A is the resulting extracted ion current chronogram for propranolol and FIG. 12B is the resulting extracted ion current chronogram for verapamil. The rise and fall in signal for each compound is due to the sampling of a portion of the droplet into the exhaust conduit of the probe and on to the analysis device in this case a time of flight mass spectrometer using positive ion mode ESI. The probe was operated with 800 µL/min methanol in overflow mode. The ion current for the internal standard was constant as expected while the ion current for the verapamil increased as the concentration of this compound in the droplets analyzed increased. The plot of the ratio of the integrated peak area of verapamil to propranol was curve fitted demonstrating quantitative analysis capabilities (FIG. 12C).

The system of the invention permits sampling by direct extraction by touching a surface onto the probe or liquid dome, by transfer of solid or liquid samples into the solvent dome or by capture of ablated material into the solvent dome. The probe volume in the dome provides for analyte dilution and extended analysis time. The volume of the dome will change with solvent composition and surface tension and with the relative positions of the liquid supply and exhaust conduits. The dome insures very effective transfer of sample material into the probe.

Ranges: throughout this disclosure, various aspects of the invention can be presented in a range format. It should be understood that the description in the range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range for example, 1, 2, 2.7, 3, 4, 5, 5.3 and 6. This applies regardless of the bread of the range.

This invention can be embodied in other forms without departing from the spirit or essential attributes thereof, and accordingly, reference should be had to the following claims to determine the scope of the invention.

I claim:

1. A system for analyzing droplets, comprising:
a probe comprising an outer probe housing having an open end; a liquid supply conduit within the housing and having an outlet positioned to deliver liquid to the open end of the housing, the liquid supply conduit being connectable to a liquid supply for delivering a liquid at a first volumetric flow rate to the open end of the housing, and a liquid exhaust conduit within the housing for removing liquid from the open end of the housing;
a liquid exhaust system in fluid connection with the liquid exhaust conduit for removing liquid from the liquid exhaust conduit at a second volumetric flow rate, wherein the liquid exhaust conduit comprises a tubular conduit positioned within the outer probe housing, and wherein the liquid supply conduit is defined by the annular space between the liquid exhaust conduit and an inner wall of the outer probe housing, wherein the position of the liquid exhaust conduit in the outer probe housing is variable;
a droplet dispenser that dispenses drops of a liquid sample or a sample-containing solvent into the liquid at the open end of the housing;
a chemical analysis device that receives the liquid from the liquid exhaust conduit;
wherein during operation of the system, the open end receives the liquid from the liquid supply conduit at the first volumetric flow rate and the liquid is drawn into and through the liquid exhaust conduit at the second volumetric flow rate, and wherein the open end receives the drops from the droplet dispenser into the liquid.

2. The system of claim 1 wherein during operation of the system the first volumetric flow rate exceeds the second volumetric flow rate and wherein the probe further comprises a liquid collection overflow system.

3. The system of claim 2 wherein the liquid collection overflow system collects an overflow liquid and directs the overflow liquid to the chemical analysis device.

4. The system of claim 1 wherein during operation of the system the first volumetric flow rate and the second volumetric flow rate are balanced.

5. The system of claim 1 wherein the droplet dispenser injects the sample or the sample-containing solvent into the open end.

6. A method for analyzing droplets, comprising:
providing a probe comprising an outer probe housing having an open end;
providing a liquid supply conduit within the outer probe housing having an outlet positioned to deliver liquid to the open end of the outer probe housing, the liquid supply conduit being connected to a liquid supply for delivering a liquid at a first volumetric flow rate to the open end of the outer probe housing, and a liquid exhaust conduit within the outer probe housing for removing liquid from the open end of the outer probe housing, wherein the liquid exhaust conduit comprises a tubular conduit positioned within the outer probe housing, and wherein the liquid supply conduit is defined by the annular space between the liquid exhaust conduit and an inner wall of the outer probe housing and wherein the position of the liquid exhaust conduit within the outer probe housing is variable;
providing a liquid exhaust system in fluid connection with the liquid exhaust conduit for removing liquid from the liquid exhaust conduit at a second volumetric flow rate;
providing a droplet dispenser for dispensing drops of a liquid sample or a sample-containing solvent into the liquid at the open end of the housing;
providing a chemical analysis instrument;
flowing liquid through the liquid supply conduit at the first volumetric flow rate to the open end and drawing the liquid into and through the liquid exhaust conduit at the second volumetric flowrate;
dispensing the drops from the droplet dispenser into the liquid at the open end;
varying the position of the liquid exhaust conduit within the outer probe housing to control dilution of the liquid sample or the sample-containing solvent in the liquid; and
analyzing the liquid from the liquid exhaust conduit in the chemical analysis instrument.

7. The method of claim 6 wherein the first volumetric flow rate exceeds the second volumetric flow rate and wherein the probe further comprises a liquid collection overflow system.

8. The method of claim 7 wherein the liquid collection overflow system collects an overflow liquid and directs the overflow liquid to the chemical analysis instrument.

9. The method of claim 6 wherein the first volumetric flow rate and the second volumetric flow rate are balanced.

10. The method of claim 6 wherein the droplet dispenser injects the drops into the open end.

11. The system of claim 1 wherein the chemical analysis device comprises an ionization source.

12. The system of claim 11 wherein the ionization source comprises an electrospray ionization source.

13. The system of claim 1 wherein the chemical analysis device comprises a mass spectrometer.

14. The system of claim 13 wherein the mass spectrometer comprises a sector time-of-flight.

15. The system of claim 13 wherein the mass spectrometer comprises a quadrupole mass filter.

16. The method of claim 6 wherein the chemical analysis instrument comprises an ionization source.

17. The method of claim 16 wherein the ionization source comprises an electrospray ionization source.

18. The method of claim 16 wherein the chemical analysis instrument also comprises a mass spectrometer.

19. The system of claim 18 wherein the mass spectrometer comprises a sector time-of-flight.

20. The system of claim 18 wherein the mass spectrometer comprises a quadrupole mass filter.

* * * * *